United States Patent [19]
Simon et al.

[11] Patent Number: 6,069,279
[45] Date of Patent: May 30, 2000

[54] PREPARATION OF SUBSTITUTED AROMATIC AMINES

[76] Inventors: Mark W. Simon, 635 Camp Dixie Rd., Pascoag, R.I. 02859; Mohammad A. Khan, 22 Evergreen Ave. Apt. #C10, Hartford, Conn. 06105

[21] Appl. No.: 09/332,304

[22] Filed: Jun. 14, 1999

[51] Int. Cl.⁷ .................................................. C07C 211/00
[52] U.S. Cl. .......................... 564/433; 564/434; 564/442; 564/163
[58] Field of Search ................... 564/433, 434, 564/442, 163

[56] References Cited

U.S. PATENT DOCUMENTS

| | | |
|---|---|---|
| 3,336,386 | 8/1967 | Dovell et al. . |
| 4,723,040 | 2/1988 | Batorewicz . |
| 4,814,504 | 3/1989 | Malz, Jr. . |
| 5,117,063 | 5/1992 | Stern et al. . |
| 5,310,491 | 5/1994 | Downs et al. . |
| 5,420,354 | 5/1995 | Malz et al. . |
| 5,453,541 | 9/1995 | Stern et al. . |
| 5,574,187 | 11/1996 | Malz et al. . |
| 5,608,111 | 3/1997 | Stern et al. . |
| 5,689,007 | 11/1997 | Malz et al. . |
| 5,728,882 | 3/1998 | Wheeler et al. . |
| 5,739,403 | 4/1998 | Reinartz et al. . |
| 5,840,982 | 11/1998 | Reynolds et al. . |
| 5,858,321 | 1/1999 | Wheeler et al. . |

FOREIGN PATENT DOCUMENTS

| | | |
|---|---|---|
| 138524 | 4/1970 | Czech Rep. . |
| 0 261 096 | 3/1988 | European Pat. Off. . |
| 0 272 238 | 6/1988 | European Pat. Off. . |
| 1 400 767 | 7/1975 | United Kingdom . |

*Primary Examiner*—Paul J. Killos
*Attorney, Agent, or Firm*—Raymond D. Thompson; Peter Dilworth

[57] ABSTRACT

A method for the preparation of aromatic amines such as N-phenyl-p-phenylenediamine wherein an aromatic amine such as aniline is oxidized with oxygen or hydrogen peroxide in the presence of a metal pentacyano ferrate(II) complex, includes subsequent catalytic reduction of the complex by hydrogenation in the presence of a metal catalyst having at least two Group VIII metals, preferably platinum in combination with ruthenium either together on a single carbon support or each metal separately on carbon supports.

23 Claims, No Drawings

PREPARATION OF SUBSTITUTED AROMATIC AMINES

BACKGROUND OF THE INVENTION

1. Technical Field

The present invention relates to a catalytic method for the production of phenyl-p-phenylenediamine (PPDA) and higher amines.

2. Background of the Related Art

The production of p-phenylenediamine and its derivatives is widespread and its uses are widely known. U.S. Pat. No. 5,117,063 discloses various methods of preparing N-phenyl-p-phenylenediamine wherein aniline and nitrobenzene are reacted under specific conditions.

In other publications, the oxidative dimerization of aniline to produce N-phenyl-p-phenylenediamine is disclosed. British patent No. 1,400,767 and European Patent 261,096 utilize an alkali metal ferricyanide whereas European Patent 272,238 utilizes a hypohalite oxidizing agent. None of these processes are very selective, nor do they give good conversions.

U.S. Pat. No. 5,858,321 discloses the use of the trisodium pentacyanoaminoferrate (II) complex to achieve improved stoichiometry in the production of PPDA. More particularly, this patent discloses the preparation of PPDA and higher amines of formula (A):

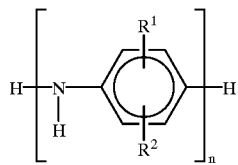

from aromatic amines of formula (B):

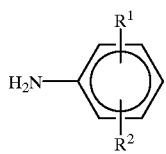

(B)

wherein n equals 2 to 5, and $R_1$ and $R_2$ are as set forth below, $R_1$ and $R_2$ may be the same or different, must be ortho or meta to the amino group, and may be hydrogen, $C_1$-$C_4$ alkyl, $C_1$-$C_4$ alkoxy, halogen, cyano, carboxylate salts amides of carboxylic acids or mixtures thereof.

In one method described therein, the presence of trisodium pentacyano ferrate(II) complexes containing various water soluble ligands, such as ammonia, mono alkyl amine, dialkyl amines, and trialkl amines, and utilizing oxygen or hydrogen peroxide as the oxidizing agents. The complex is then reduced by hydrogeneration using suitable metal catalysts.

There yet remains need for improvement in processes to produce PPDA. In particular, current catalytic processes suffer from catalyst poisoning and excessive catalyst usage.

SUMMARY OF THE INVENTION

A method is provided herein for the preparation of substituted aromatic amine of formula (A):

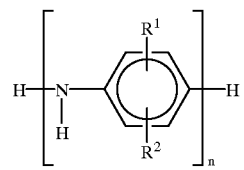

wherein $R^1$ and $R^2$ may be the same or different substituents, ortho or meta to the amino group, selected from the group consisting of hydrogen, $C_1$-$C_4$ alkyl, $C_1$-$C_4$ alkoxy, halogen, cyano, carboxylate salts and amides of carboxylic acids or mixtures thereof, and n is 2 to 5, the method comprising:

a) oxidizing a solution of an aromatic amine of formula (B):

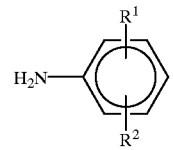

wherein $R^1$ and $R^2$ have the aforestated meanings in the presence of an oxidizing agent and a metal pentacyano ferrate(II) complex of a water soluble type having water soluble ligands as part of the complex to provide an arylenediaminopentacyano ferrate complex; and, b) reducing said arylenediaminopentacyano ferrate complex with a reducing agent in the presence of a catalyst having at least two metals selected from Group VIII of the Periodic Table of the Elements to provide substituted aromatic amine (A).

The method described herein advantageously employs a poison-resistant catalyst which can be used at very low levels to provide an economically viable process to produce N-phenyl-p-phenylenediamine via the oxidative dimerization of aniline.

DETAILED DESCRIPTION OF PREFERRED EMBODIMENTS

A preferred method of the present invention for producing N-phenyl-p-phenylenediamine (PPDA) involves the steps of (a) oxidizing aromatic amine (B) in the presence of trisodium pentacyano ferrate(II) complexes and an oxidizing agent to provide an N-phenyl-p-phenylenediamo-pentacyano ferrate complex followed by (b) reduction of the N-phenyl-p-phenylenediamino-pentacyano ferrate complex with a reducing agent in the presence of a multiple metal catalyst as hereinafter more fully described.

In the first step, any suitable oxidizing agent including either oxygen or hydrogen peroxide may be used as the oxidizing agent. Oxygen is the preferred oxidizing agent. Still more preferred is the use of oxygen under pressure which will increase the rate of oxidation and facilitate the completion of step (a).

Ordinarily, the amount of oxidizing agent can range from about 1 mole to about 10 moles and preferably from about 1 mole to about 2 moles based on the moles of aromatic amine (B). Oxygen, when employed as the oxidizing agent, can be provided at a pressure ranging from about 1 atm to about 70 atm.

The metal pentacyano ferrate(II) complexes useful in this invention must be of a water soluble type having water soluble ligands as a part of the complex. Such complexes have the general formula $M_3[Fe(CN)_5Y].xH_2O$, wherein x equals about 3 to about 6. M is a metal, preferably an alkali metal, and most preferably sodium or potassium. Y is a water soluble ligand such as ammonia, mono alkyl amines such as methyl, ethyl, propyl, or butyl amines, dialkyl amines such as dimethyl or diethyl amine and trialkyl amines such as trimethyl amine or triethyl amine. Other amines that can be used are N,N-dimethylaminoethanol, N,N,N',N'-tetramethylethylenediamine, and substituted or unsubstituted pyridine. A variety of other ligands can be used, limited only by their solubility, and their ability to be displaced by aniline and by their stability. A preferred structure for this preferred complex is $Na_3[Fe(CN)_5 NH_3].xH_2O$, or its dimer. Sodium pentacyano ferrates(II) containing ligands other than ammonia can be prepared by substitution of the ammonia complex with an excess of the appropriate ligand.

Ordinarily, the amount of pentacyano ferrate (II) complex can range from about 0.10 mole to about 10.0 moles per mole of amine, most preferably from about 0.5 moles to about 1.0 moles.

In the second step of the preferred reaction, the N-phenyl-p-phenylenediamo-pentacyano ferrate complex is reduced with a reducing agent such as hydrogen or hydrazine using a heterogeneous multiple metal, especially bimetallic, catalyst. This catalyst is selected from the metals of Group VIII of the Periodic Table of the Elements (CAS version) such as palladium, platinum, ruthenium, or rhodium. The catalyst may or may not be supported. If supported, the supports may be carbon, alumina, silica, silicoaluminates and the like, many of which are known to those familiar with the art.

The mixture of aniline and PPDA, which is the product of the reaction, is extracted with a suitable solvent. Then the heterogeneous catalyst is filtered off. Suitable solvents include those that are water-immiscible and easily recyclable. The aqueous layer containing the sodium pentacyano amino ferrate(II) complex is then recycled.

The compounds of this invention can be synthesized advantageously by the following general method. The preferred method for the preparation of PPDA is contained in the examples that follow.

The first step of a preferred process of this invention involves dissolving sodium pentacyanoamino ferrate(II) in water, preferably in a concentration range of from about 10% to about 25%. The synthesis of sodium pentacyanoamino ferrates(II) are known. They can be prepared according to the method of G. Brauer "Handbook of Preparative Inorganic Chemistry", 2nd ed. Vol II, Academic Press, New York, N.Y., (1965)p. 1511.

An alternate method for preparation of trisodium pentacyanoamino ferrate(II) is the concurrent addition of aqueous solution of ferrous chloride or ferrous sulfate, preferably stabilized with hypophosphorous acid, and sodium cyanide in the ratio of 1 to 5 equivalents to an aqueous solution of ammonium hydroxide. The reaction mixture is continuously stirred and maintained preferably at a temperature of from about 0° C. to about 30° C., most preferably about 10 °C. to about 15° C. The aqueous solution of ammonium hydroxide may contain anywhere from one equivalent based on the ferrous chloride or ferrous sulfate to a large excess. The preferred range is two to ten equivalents and the most preferred is six to ten equivalents of ammonium hydroxide.

The concurrent additions are done over one to three hours and the solution is then filtered if necessary to remove small amounts of iron hydroxides and the complex may be precipitated by adding isopropanol or any convenient water soluble organic solvent. The complex may be dried or redissolved in water without drying and used directly. The excess ammonia and isopropanol are recovered.

For the addition of aniline, a water miscible organic solvent may be added to help solubilize the aniline. In the instant invention, this reaction may be run without organic solvent. Examples of such solvents are ethylene glycol, propylene glycol, diethylene glycol, and triethylene glycol.

Two moles of aniline per mole of active complex are added and the mixture is then oxidized. Oxygen or hydrogen peroxide are two possible oxidizing agents that can be used. The oxidation reaction is preferably carried out at a temperature of from about 5° C. to about 70° C., more preferably about 15° C. to about 50° C., and at an oxygen pressure of from about 30 psig to about 1,000 psig, more preferably from about 200 psig to about 1,000 psig.

In the second step of the process of this invention, the oxidized complex containing the N-phenyl-p-phenylenediamino ligand is subjected to reduction in the presence of a heterogeneous multiple metallic catalyst (described below). Suitable reducing agents include, for example, hydrogen and hydrazine. Since hydrogen is preferred the reduction hereinafter will be described in terms of hydrogenation. This may be carried out without added solvent, or in the presence of a suitable water immiscible solvent. Possible solvents in this category include butyl acetate, hexanol, 2-ethyl-1-butanol, hexyl acetate, ethyl butyl acetate, amyl acetate, or aniline and the like. After hydrogenation, the heterogeneous catalyst is removed by filtration and the organic layer separated. The solvent, aniline, and N-phenyl-p-phenylenediamine are recovered by distillation. The sodium pentacyanoamino ferrate complex is then recycled.

The pH is adjusted as necessary with the ligand used. This adjustment of pH is achieved by the addition of any appropriate acid, for example, acetic acid or with the ligand used in the complex. The pH of the complex can be varied from 8.0 to 13.0. A more preferred range of pH is from 10 and 12.

Hydrogen pressures may be in the range of from about 1 atmosphere to 100 atmospheres, or about 14.7 to 1,470 psig. A preferred range of these pressures would be from about 2 to about 75 atmospheres, or about 30 to 1,000 psig.

Hydrogenation temperatures may range from about 5° C. to about 70° C., preferably about 5° C. to about 50° C., most preferred about 25° C. to about 50° C. The temperature used will require a balance of factors to maximize the reaction rate and yield of the process. Higher temperatures will slowly degrade the complex. Low temperatures reduce the solubility of the complex and decrease the rate of reaction.

The catalyst used in the present invention contains at least two different Group VIII metals, either independently on supports such as carbon or a bimetallic on a single support. Particularly preferred is platinum in combination with ruthenium. Metal ratios of Pt to Ru can range from about 0.5:1 to about 10:1, preferably about 0.4:1 to about 3:1. The amount of catalyst employed herein, calculated as the total weight of all Group VIII metal species, can generally range from about 50 mg to about 1,000 mg, preferably from about 150 mg to about 700 mg and more preferably from about 100 mg to about 300 mg, per kg of aromatic amine reactant (B). It has been found that ruthenium is an effective metal for selectively absorbing catalyst poisons such as sodium nitroprusside and nitrogen oxide type impurities that might be generated by the oxidation of ammonia in the oxidation reaction. Furthermore, ruthenium may be an electron donor to the pentacyanoamino ferrate complex to facilitate the reduction. It has also been found that activating ruthenium can be more easily achieved in a multiple metal catalyst. As shown below, catalyst levels can be lowered by 300% or more by using the Pt/Ru bimetallic catalyst as opposed to monometal Pt or Pd catalyst.

The catalyst metal may be unsupported or, more preferably, supported on a conventional support such as carbon, alumina, silica, silicoaluminates and the like. Activated carbon is preferred. Optionally, the bimetallic catalyst herein can be employed in the oxidation step of the reaction.

Comparative Examples 1 to 4 are illustrative of the prior art (in the use of monometallic catalysts) and Examples 1 to 7 illustrate the method of the invention.

GENERAL CONDITIONS

Reduction reactions described below are carried out at 50° C. and 1000 psig hydrogen in a 1-L batch reactor. An agitation rate of 1400 rpms is used. Butyl acetate was used as a solvent, although hexanol is believed to be a superior solvent. Bimetallic catalysts of varying Pt:Ru or Pd:Ru ratios were studied and compared against conventional monometallic catalysts. Catalyst performance was evaluated based on reaction rates, susceptibility to poisoning, catalyst lifetime, and poison resistance. The reaction was monitored using UV-visible spectroscopic analysis The sodium pentacyano (N-phenyl-phenylenediamine) iron(III) intermediate was monitored at a maximum absorbance of 660 nm. The sodium pentacyanoamino ferrate (II) or sodium pentacyanoanilino ferrate(II) complex in the reduced form was monitored at a maximum absorbance of 400 nm. Both the aniline and amino cyano-iron(II) complex have maximum absorbances at 400 nm. Reaction rates were determined by recording spectroscopic measurements at 10 minutes intervals until the reaction was complete. The reaction rates for seven different metal catalysts are shown in Table 1. The reaction rates for five different catalysts containing various Pt:Ru metal ratios are shown in Table 2.

COMPARATIVE EXAMPLE 1

The oxidative dimerization of aniline was studied using 5% Pd/C as the heterogeneous catalyst in the reduction reaction. Oxygen was used as the oxidizing agent. The oxidation reaction was carried out in a 1-L stainless steel autoclave using 50.0 g of aniline, 30.0 g of sodium pentacyanoaminoferrate(II), 4.5 g sodium chloride, 270 g deionized water and 1000 psig oxygen at 50° C. for 15 minutes. The oxidized sodium pentacyano(N-phenyl-p-phenylenediamine) ferrate intermediate was removed from the reactor and pumped into a second 1-L vessel containing 0.050 g 5% palladium-on-carbon catalyst and 265 g butyl acetate, 48 g aqueous ammonium hydroxide at 1000 psig hydrogen pressure and 50° C. The reaction reached 99.0% completion in 240 minutes.

COMPARATIVE EXAMPLE 2

The oxidative dimerization of aniline was studied using 4% Pt/C as the heterogeneous catalyst in the reduction reaction. Oxygen was used as the oxidizing agent. The oxidation reaction was carried out in a 1-L stainless steel autoclave using 50.0 g of aniline, 30.0 g of sodium pentacyanoaminoferrate (II), 4.5 g sodium chloride, 270 g deionized water and 1000 psig oxygen at 50° C. for 15 minutes. The oxidized sodium pentacyano(N-phenyl-p-phenylenediamine) ferrate intermediate was removed from the reactor and pumped into a second 1-L vessel containing 0.025 g 4% platinum-on-carbon catalyst and 265 g butyl acetate, 48 g aqueous ammonium hydroxide at 1000 psig hydrogen pressure and 50° C. The reaction reached 98.8% completion in 90 minutes.

COMPARATIVE EXAMPLE 3

The oxidative dimerization of aniline was studied using 5% Ru/C as the heterogeneous catalyst in the reduction reaction. Oxygen was used as the oxidizing agent. The oxidation reaction was carried out in a 1-L stainless steel autoclave using 50.6 g of aniline, 30.0 g of sodium pentacyanoamino ferrate(II), 4.5 g sodium chloride, 270 g deionized water and 1000 psig oxygen at 50° C. for 15 minutes. The oxidized sodium pentacyano(N-phenyl-p-phenylenediamine) ferrate intermediate was removed from the reactor and pumped into a second 1-L vessel containing 0.061 g 5% ruthenium-on-carbon catalyst and 265 g butyl acetate, 48 g aqueous ammonium hydroxide at 1000 psig hydrogen pressure and 50° C. The reaction reached only 39.5% completion before catalyst poisoning occurred after 120 minutes of reaction. The reaction was terminated when no hydrogen absorption and no changes in the spectroscopic analysis were observed.

COMPARATIVE EXAMPLE 4

The oxidative dimerization of aniline was studied using 4% Rh/C as the heterogeneous catalyst in the reduction reaction. Oxygen was used as the oxidizing agent. The oxidation reaction was carried out in a 1-L stainless steel autoclave using 50.6 g of aniline, 30.0 g of sodium pentacyanoamino ferrate(II), 4.5 g sodium chloride, 270 g deionized water and 1000 psig oxygen at 50° C. for 15 minutes. The oxidized sodium pentacyano(N-phenyl-p-phenylenediamine) ferrate intermediate was removed from the reactor and pumped into a second 1-L vessel containing 0.064 g 4% rhodium-on-carbon catalyst and 265 g butyl acetate, 48 g aqueous ammonium hydroxide at 1000 psig hydrogen pressure and 50° C. The reaction reached 98.2% completion in 220 minutes.

EXAMPLE 1

The oxidative dimerization of aniline was studied using 5% Pd/1%Ru/C as the heterogeneous catalyst in the reduction reaction. Oxygen was used as the oxidizing agent. The oxidation reaction was carried out in a 1-L stainless steel autoclave using 50.6 g of aniline, 30.0 g of sodium pentacyanoamino ferrate (II), 4.5 g sodium chloride, 270 g deionized water and 1000 psig oxygen at 50° C. for 15 minutes. The oxidized sodium pentacyano(N-phenyl-p-phenylenediamine) ferrate intermediate was removed from the reactor and pumped into a second 1-L vessel containing 0.055 g 5% palladium/1% ruthenium-on-carbon catalyst and 265 g butyl acetate, 48 g aqueous ammonium hydroxide at 1000 psig hydrogen pressure and 50° C. The reaction reached 99.2% completion in 240 minutes.

EXAMPLE 2

The oxidative dimerization of aniline was studied using 4% Pt/3%Ru/C as the heterogeneous catalyst in the reduction reaction. Oxygen was used as the oxidizing agent. The oxidation reaction was carried out in a 1-L stainless steel autoclave using 50.6 g of aniline, 30.0 g of sodium pentacyanoamino ferrate(II), 4.5 g sodium chloride, 270 g deionized water and 1000 psig oxygen at 50° C. for 15 minutes. The oxidized sodium pentacyano(N-phenyl-p- phenylenediamine) ferrate intermediate was removed from the reactor and pumped into a second 1-L vessel containing 0.009 g 4% platinum/3% ruthenium-on-carbon catalyst and 265 g butyl acetate, 48 g aqueous ammonium hydroxide at 1000 psig hydrogen pressure and 50° C. The reaction reached 99.2% completion in 60 minutes.

EXAMPLE 3

The oxidative dimerization of aniline was studied using 2.5% Pt/3.75%Ru/C as the bimetallic heterogeneous catalyst in the reduction reaction. Oxygen was used as the oxidizing agent. The oxidation reaction was carried out in a 1-L stainless steel autoclave using 50.6 g of aniline, 30.0 g of sodium pentacyanoamino ferrate(II), 4.5 g sodium chloride, 270 g deionized water and 1000 psig oxygen at 50° C. for 15 minutes. The oxidized sodium pentacyano(N-phenyl-p-phenylenediamine) ferrate intermediate was removed from the reactor and pumped into a second 1-L vessel containing 0.014 g 2.75% platinum/3.5% palladium-on-carbon catalyst and 265 g butyl acetate, 48 g aqueous ammonium hydroxide at 1000 psig hydrogen pressure and 50° C. The reaction reached 99.0% completion in 70 minutes.

EXAMPLE 4

The oxidative dimerization of aniline was studied using 2.5% Pt/3.0%Ru/C as the bimetallic heterogeneous catalyst in the reduction reaction. Oxygen was used as the oxidizing agent. The oxidation reaction was carried out in a 1-L stainless steel autoclave using 50.6 g of aniline, 30.0 g of sodium pentacyanoamino ferrate (II), 4.5 g sodium chloride, 270 g deionized water and 1000 psig oxygen at 50° C. for 15 minutes. The oxidized sodium pentacyano(N-phenyl-p-phenylenediamine) ferrate intermediate was removed from the reactor and pumped into a second 1-L vessel containing 0.014 g 2.75% platinum/3.0% palladium-on-carbon catalyst and 265 g butyl acetate, 48 g aqueous ammonium hydroxide at 1000 psig hydrogen pressure and 50° C. The reaction reached 98.9% completion in 70 minutes.

EXAMPLE 5

The oxidative dimerization of aniline was studied using 3.0% Pt/1.0%Ru/C as the bimetallic heterogeneous catalyst in the reduction reaction. Oxygen was used as the oxidizing agent. The oxidation reaction was carried out in a 1-L stainless steel autoclave using 50.6 g of aniline, 30.0 g of sodium pentacyanoamino ferrate(II), 4.5 g sodium chloride, 270 g deionized water and 1000 psig oxygen at 50° C. for 15 minutes.

The oxidized sodium pentacyano(N-phenyl-p-phenylenediamine) ferrate intermediate was removed from the reactor and pumped into a second 1-L vessel containing 0.012 g 3.0% platinum/1.0% palladium-on-carbon catalyst and 265 g butyl acetate, 48 g aqueous ammonium hydroxide at 1000 psig hydrogen pressure and 50° C. The reaction reached 99.7% completion in 40 minutes.

EXAMPLE 6

The oxidative dimerization of aniline was studied using 3.0% Pt/2.0%Ru/C as the bimetallic heterogeneous catalyst in the reduction reaction. Oxygen was used as the oxidizing agent. The oxidation reaction was carried out in a 1-L stainless steel autoclave using 50.6 g of aniline, 30.0 g of sodium pentacyanoamino ferrate(II), 4.5 g sodium chloride, 270 g deionized water and 1000 psig oxygen at 50° C. for 15 minutes. The oxidized sodium pentacyano(N-phenyl-p-phenylenediamine) ferrate intermediate was removed from the reactor and pumped into a second 1-L vessel containing 0.012 g 3.0% platinum/2.0% palladium-on-carbon catalyst and 265 g butyl acetate, 48 g aqueous ammonium hydroxide at 1000 psig hydrogen pressure and 50° C. The reaction reached 99.2% completion in 60 minutes.

EXAMPLE 7

The oxidative dimerization of aniline was studied using 4.0% Pt/3.0%Ru/C as the bimetallic heterogeneous catalyst in the reduction reaction. Oxygen was used as the oxidizing agent. The oxidation reaction was carried out in a 1-L stainless steel autoclave using 50.6 g of aniline, 30.0 g of sodium pentacyanoamino ferrate(II), 4.5 g sodium chloride, 270 g deionized water and 1000 psig oxygen at 50° C. for 15 minutes. The oxidized sodium pentacyano(N-phenyl-p-phenylenediamine) ferrate intermediate was removed from the reactor and pumped into a second 1-L vessel containing 0.009 g 4.0% platinum/3.0% palladium-on-carbon catalyst and 265 g butyl acetate, 48 g aqueous ammonium hydroxide at 1000 psig hydrogen pressure and 50° C. The reaction reached 98.2% completion in 70 minutes.

TABLE 1

| EXAMPLE | CATALYST | LOADING (g)[a] | REACTION TIME (min) | PERCENT COMPLETE[b] |
| --- | --- | --- | --- | --- |
| Comp Ex 1 | 5% Pd/C | 0.050 | 240 | 99.0 |
| Comp Ex 2 | 4% Pt/C | 0.025 | 90 | 98.9 |
| Comp Ex 3 | 5% Ru/C | 0.061 | 120 | 39.5 |
| Comp Ex 4 | 4% Rh/C | 0.064 | 220 | 98.2 |
| 1 | 5% Pd/1% Ru/C | 0.055 | 240 | 99.2 |
| 2 | 4% Pt/3% Ru/C | 0.009 | 60 | 99.2 | a: grams of dry catalyst
b: UV-Visible spectroscopic measurement

As these data show, Example 2 achieved 99.2% completion in only 60 minutes compared with 240 minutes for Comparative Example 1 and employed only about 35% as much catalyst as Comparative Example 2.

TABLE 2

| EXAMPLE | CATALYST: Pt/Ru/C | | LOADING (g)[a] | REACTION TIME (min) | PERCENT COMPLETE[b] |
| --- | --- | --- | --- | --- | --- |
| | Pt (wt %) | Ru (wt %) | | | |
| 3 | 2.5 | 3.75 | 0.014 | 70 | 99.0 |
| 4 | 2.5 | 3.0 | 0.014 | 70 | 98.9 |
| 5 | 3.0 | 1.0 | 0.012 | 40 | 99.7 |
| 6 | 3.0 | 2.0 | 0.012 | 60 | 99.2 |
| 7 | 4.0 | 3.0 | 0.009 | 70 | 98.2 | a: grams of dry catalyst
b: UV-Visible spectroscopic measurements

Examples 3 to 7 demonstrate that use of the bimetallic Pt/Ru on carbon catalyst in various Pt:Ru ratios achieves superior results as compared with use of either Pt or Ru alone. For example, in Example 4 the bimetallic catalyst (2.5% Pt/3.0% Ru/C) achieved 98.9% completion in 70 minutes with a catalyst loading of only 0.014 g, whereas the 4% Pt/C monometallic catalyst of comparative Example 2 required 90 minutes to achieve the same percentage of completion with a catalyst loading of 0.025 g. The 5% Ru/C catalyst of Comparative Example 3 at a loading of 0.061 gram required 120 minutes to achieve a 39.5% completion.

EXAMPLE 8

The oxidative dimerization of aniline was studied using two individual heterogeneous catalysts on independent supports in the reduction reaction. Oxygen was used as the oxidizing agent. The oxidation reaction was carried out in a 1-L stainless steel autoclave using 14.1 g of aniline, 33.2 g of sodium pentacyanoamino ferrate (II), 12.4 g of sodium sulfate powder, 220 g deionized water and 1000 psig oxygen at 50° C. for 15 minutes. The oxidized sodium pentacyano (N-phenyl-p-phenylenediamine) ferrate intermediate was removed from the reactor and pumped into a second 1-L vessel containing 0.008 g 4% platinum-on-carbon and 0.0005 g 5% ruthenium-on-carbon catalysts and 200 g of 1-hexanol, 52.8 g aqueous ammonium hydroxide (28%) at 1000 psig hydrogen pressure and 50° C. The reaction reached 98.4% completion after 70 minutes.

EXAMPLE 9

The oxidative dimerization of aniline was studied using two individual heterogeneous catalysts on independent supports in the reduction reaction. The dual catalyst system consisted of a physical mixture of 4% platinum-on-carbon and 5% ruthenium-on-carbon catalysts. Oxygen was used as the oxidizing agent. The oxidation reaction was carried out in a 1-L stainless steel autoclave using 14.1 g of aniline, 33.2 g of sodium pentacyanoamino ferrate (II), 12.4 g of sodium sulfate powder, 220 g deionized water and 1000 psig oxygen at 50° C. for 15 minutes. The oxidized sodium pentacyano (N-phenyl-p-phenylenediamine) ferrate intermediate was removed from the reactor and pumped into a second 1-L vessel containing 0.008 g 4% platinum-on-carbon and 0.015 g 5% ruthenium-on-carbon catalysts and 200 g of 1-hexanol, 52.8 g aqueous ammonium hydroxide (28%) at 1000 psig hydrogen pressure and 50° C. The reaction reached 98.9% completion after 60 minutes.

TABLE 3

| Ex. | CATALYST: Pt/C + Ru/C physical mixture Pt (wt %) | Ru (wt %) | LOADING (g)[a] Pt/C (g) | Ru/C (g) | Pt:Ru Ratio | REAC- TION TIME (min) | PER- CENT COM- PLETE[b] |
|---|---|---|---|---|---|---|---|
| 8 | 4.0 | 5.0 | 0.008 | 0.005 | 1.3 | 70 | 98.4 |
| 9 | 4.0 | 5.0 | 0.008 | 0.015 | 0.4 | 60 | 98.9 | a: grams of dry catalyst
b: UV-Visible spectroscopic measurements

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A method for the preparation of substituted aromatic amines of formula (A)

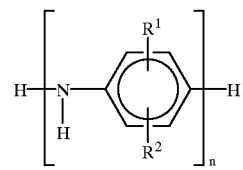

(A)

wherein $R_1$ and $R^2$ can be the same or different substituents, ortho or meta to the amino group, and are selected from the group consisting of hydrogen, $C_1$–$C_4$ alkyl, $C_1$–$C_4$ alkoxy, halogen, cyano, carboxylate salts, amides of carboxylic acids and mixtures thereof, and n is 2 to 5, the method comprising the steps of:

a) oxidizing a solution of an aromatic amine of formula (B)

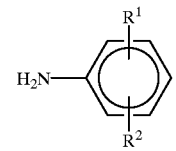

(B)

wherein $R^1$ and $R^2$ have the aforesaid meanings in the presence of an oxidizing agent and a metal pentacyano ferrate(II) complex of a water soluble type having water soluble ligands as part of the complex to form an arylenediaminopentacyano ferrate complex; and b) reducing said arylenediaminopentacyano ferrate complex with a reducing agent in the presence of a catalyst having at least two metals selected from Group VIII of the Periodic Table of the Elements to provide the substituted aromatic amine of formula (A).

2. The method of claim 1 wherein the Group VIII metals of the catalyst are at least two metals selected from the group consisting of palladium, platinum, ruthenium, and rhodium.

3. The method of claim 2 wherein at least one of said metals is ruthenium.

4. The method of claim 1 wherein said catalyst is a bimetallic catalyst containing ruthenium and platinum.

5. The method of claim 4 wherein the ratio of platinum to ruthenium ranges from about 0.5:1 to about 10:1 by weight.

6. The method of claim 4 wherein the ratio of platinum to ruthenium ranges from about 0.8:1 to about 3:1 by weight.

7. The method of claim 1 wherein the catalyst includes a catalyst support.

8. The method of claim 7 wherein the catalyst support is carbon.

9. The method of claim 8 wherein the metal content of the supported catalyst ranges from about 1% to about 10% by weight.

10. The method of claim 1 wherein the oxidizing agent is oxygen or hydrogen peroxide.

11. The method of claim 1 wherein the oxidizing agent is oxygen and the reducing agent is hydrogen, wherein the oxygen is used under pressure ranging from about 1 atmosphere to about 100 atmospheres.

12. The method of claim 11 wherein the oxygen in the oxidizing step and the hydrogen in the reducing step are under pressures independently selected and ranging from about 2 atmospheres to about 75 atmospheres.

13. The method of claim 1 wherein the metal pentacyano ferrate (II) complex has the formula $M_3[Fe(CN)_5Y].x H_2O$, wherein M is an alkali metal, Y is a water soluble ligand selected from the group consisting of ammonia, monoalkylamine, dialkylamine and trialkylamine, and X is 3 to 6.

14. The method of claim 1 wherein the metal pentacyano ferrate(II) complex is a sodium pentacyano ferrate(II) complex containing water soluble ligands selected from the group consisting of ammonia, monoalkyl amines, dialkyl amines, trialkyl amines, N,N-dimethylaminoethanol, N,N,N',N'-tetramethylethylenediamine and pyridine.

15. A method for producing N-phenyl-p-phenylenediamine comprising the steps of:
   a) oxidizing aniline in the presence of oxygen and trisodium pentacyano ferrate(II) complex to form an N-phenyl-p-phenylenediaminopentacyano ferrate complex; and
   b) reducing the N-phenyl-p-phenylenediaminopentacyano ferrate complex with hydrogen and a catalyst containing platinum and ruthenium to yield N-phenyl-p-phenylenediamine.

16. The method of claim 15 wherein the ratio of platinum to ruthenium in the catalyst ranges from about 0.5:1 to about 10:1 by weight.

17. The method of claim 15 wherein the ratio of platinum to ruthenium in the catalyst ranges from about 0.8:1 to about 3:1 by weight.

18. The method of claim 15 wherein the catalyst includes a catalyst support to form a supported catalyst.

19. The method of claim 18 wherein the catalyst support is carbon.

20. The method of claim 18 wherein the metal content of the supported catalyst ranges from about 1% to about 10% by weight.

21. The method of claim 1 wherein the catalyst comprises two metals selected from Group VIII of the Periodic Table of the Elements on independent supports.

22. The method of claim 1 wherein the catalyst comprises ruthenium and platinum metals on independent supports.

23. The method of claim 22 wherein the ratio of platinum to ruthenium in the catalyst ranges from about 0.4:1 to about 3:1 by weight.

* * * * *